(12) United States Patent
Fu et al.

(10) Patent No.: US 8,492,161 B2
(45) Date of Patent: Jul. 23, 2013

(54) QUANTITATIVE ANALYSIS OF A FUNCTION GROUP ON THE SURFACE OF A SOLID MATERIAL

(75) Inventors: Meng-Jun Fu, Taoyuan County (TW); Kuan-Yin Chen, Taoyuan County (TW); Chia-Chieh Chen, Taoyuan County (TW)

(73) Assignee: Atomic Energy Council—Institute of Nuclear Energy Research, Lungtan, Taoyuan (TW)

( * ) Notice: Subject to any disclaimer, the term of this patent is extended or adjusted under 35 U.S.C. 154(b) by 218 days.

(21) Appl. No.: 13/217,366

(22) Filed: Aug. 25, 2011

(65) Prior Publication Data

US 2013/0052747 A1    Feb. 28, 2013

(51) Int. Cl.
*G01N 31/16*    (2006.01)

(52) U.S. Cl.
USPC ............. 436/163; 436/45; 436/145; 436/164; 436/171

(58) Field of Classification Search
None
See application file for complete search history.

*Primary Examiner* — Robert Xu
(74) *Attorney, Agent, or Firm* — Jackson IPG PLLC

(57) ABSTRACT

Disclosed is a method for quantitatively analyzing a functional group on the surface of a solid material. The functional group is carboxylic group while the solid material is carbon nano-tubes. The carboxylic group reacts with sodium hydrogen carbonate, thus turning the carboxylic groups into sodium carboxylate while consuming the sodium ions in the solution. The carbon nano-tubes are separated from the sodium hydrogen carbonate solution. The number of the sodium ions before and after the reaction is analyzed. Moreover, the sodium carboxylate carried on the reacted carbon nano-tubes with reacts with hydrochloric acid solution, thus dissolving the sodium ions in the hydrochloric acid solution. The carbon nanotubes are separated from from the hydrochloric acid solution. The amount of the sodium ions is analyzed before and after the reaction in the hydrochloric acid solution.

4 Claims, 1 Drawing Sheet

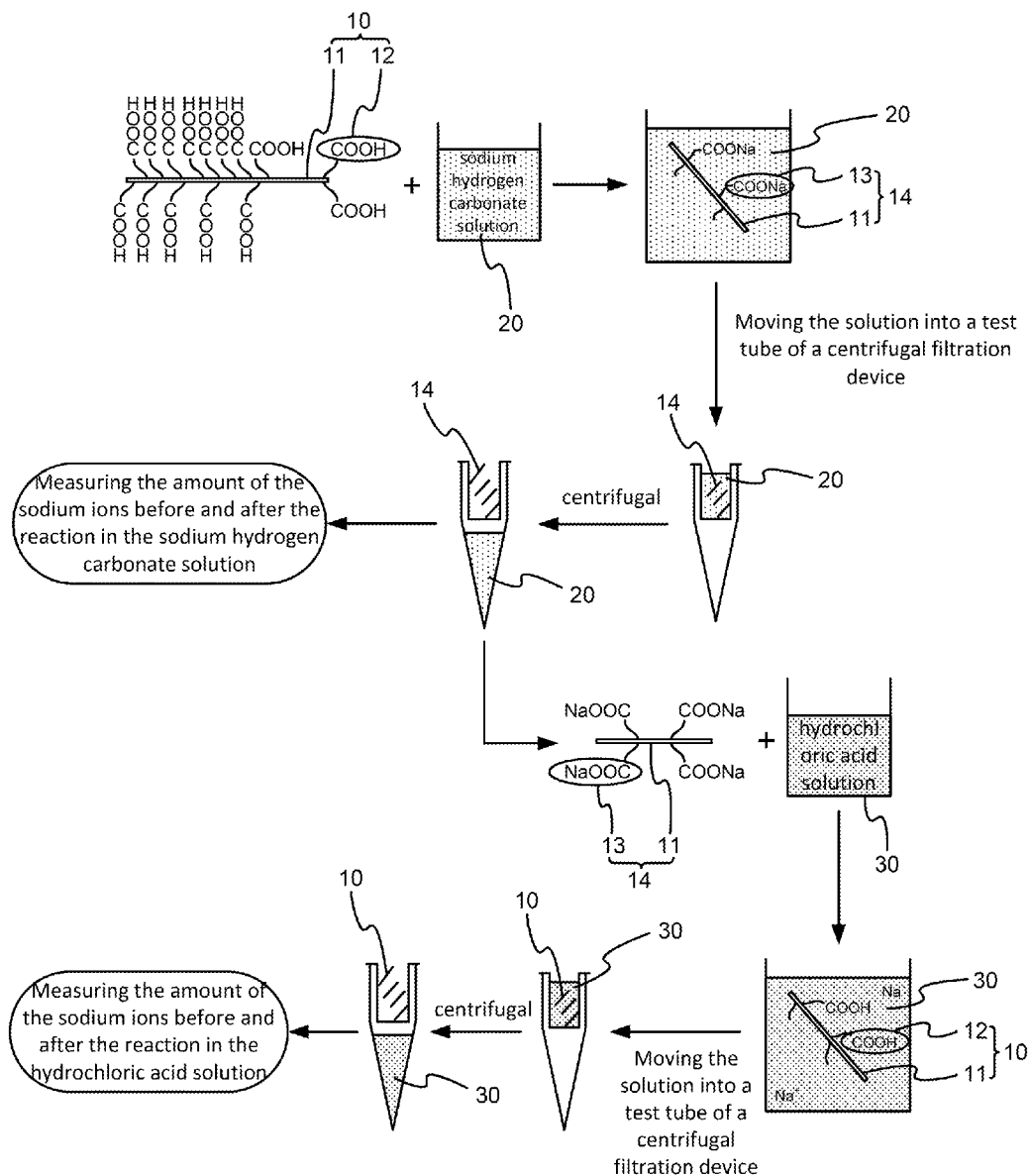

QUANTITATIVE ANALYSIS OF A FUNCTION GROUP ON THE SURFACE OF A SOLID MATERIAL

BACKGROUND OF INVENTION

1. Field of Invention

The present invention relates to a quantitative analysis of a functional group on the surface of a solid material and, more particularly, to a quantitative analysis of a functional group on the surface of a solid material based on acid-base titration.

2. Related Prior Art

Carbon nano-tubes are a new material. The carbon nano-tubes are however not directly used after they are made because they tend to tangle with one another to form masses. To distribute the carbon nano-tubes evenly in a solution or another material, they must be subjected to a chemical process to produce a functional group on their surfaces. Generally, nitric acid or sulfuric acid is used to produce carboxylic group and/or hydroxylic group on the surfaces of the carbon nano-tubes to provide the carbon nano-tubes with affinity for a dissolvent so that the carbon nano-tubes can be suspended and distributed in the dissolvent evenly. Then, the functional groups can be bonded to another chemical material. Thus, the carbon nano-tubes are suitable for various uses. The amount of the functional group on the surfaces of the carbon nano-tubes determines the amount of the chemical material that can be bonded to the carbon nano-tubes. Therefore, it is necessary to execute a quantitative analysis for the functional group.

Conventional quantitative analysis for the carboxylic group on the surfaces of the carbon nano-tubes are based on the acid-base titration. The conventional quantitative analysis is however complicated because the carbon nano-tubes possess special properties.

For example, as set forth in Equation (1), a first number (a) of moles of carboxylic group (—COOH) included in carbon nano-tubes ("CNT") is reacted with a second number (b) of moles of sodium hydrogen carbonate ($NaHCO_3$) to produce the first number (a) of moles of ($H_2CO_3$), leaving the second number minus the first number (b−a) of moles of sodium hydrogen carbonate. By sucking filtration, the carbon nano-tubes are separated from the solution. After the separation, as set forth in Equation (2), the second number (b) of moles of hydrochloric acid (HCl) is introduced into the sodium hydrogen carbonate solution so that the remaining sodium hydrogen carbonate is turned into the second number minus the first number (b−a) of moles of sodium chloride (NaCl) and the second number (2) of moles of carbonic acid, leaving the first number (a) of moles of hydrochloric acid. As set forth in Equation (3), by heating or introduction of nitrogen, the carbonic acid is turned into carbon dioxide ($CO_2$) that escapes from the solution. Then, sodium hydroxide (NaOH) is used for acid-base titration of the first number (a) of moles of hydrochloric acid. From the fact that the first number of moles of sodium hydroxide is used for the titration, it is learned that the amount of the carboxylic group is the first number (a) of moles.

The foregoing process takes a long period of time. In particular, the separation of the carbon nano-tubes from the solution takes a long period of time for several reasons. Firstly, the size of the carbon nano-tubes is in the order of a nanometer and requires a filtration film with very small bores. Secondly, the very small bores of the filtration film could easily be blocked by the carbon nano-tubes. Thirdly, the acid-base titration is not sensitive, the carbon nano-tubes do not include a lot of carboxylic group, and it requires a lot of carbon nano-tubes for experiment. Therefore, the conventional quantitative analysis takes a long period of time and requires a lot of samples.

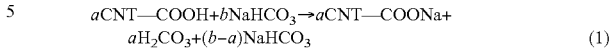

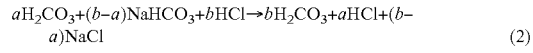

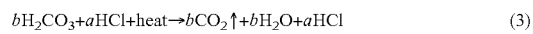

For example, 1 mole of carboxylic group included in carbon nano-tubes is reacted with 5 moles of sodium hydrogen carbonate to produce 1 mole of carbon-nano-tubes-sodium carboxylate, 4 moles of sodium hydrogen carbonate and 1 mole of carbonic acid. By sucking filtration, the carbon nano-tubes are separated from the solution. 5 moles of hydrochloric acid are introduced into the sodium hydrogen carbonate solution to produce 4 moles of sodium chloride and 5 moles of carbonic acid, with 1 mole of hydrochloric acid left. By heating, the carbonic acid is turned into carbon dioxide that escapes from the solution. Now, the solution contains 4 moles of sodium chloride and 1 mole of hydrochloric acid. Then, sodium hydroxide is used for acid-base titration of the 1 mole of hydrochloric acid that is left. From the fact that the amount of the sodium hydroxide used for the titration is 1 mole, it is learned that the amount of the carboxylic group is 1 mole.

In the conventional quantitative analysis, the amount of the sodium hydrogen carbonate must be excessive to hold the equations. Therefore, estimation must be done before the experiment. For example, 1 gram of carbon nano-tubes is used. For convenience of calculation, it is assumed that this 1 gram of carbon nano-tubes contains 100% of carboxylic group (—COOH) although the percentage cannot be 100%. 1 gram of —COOH is about 0.02222 mole. There must be provided an excessive amount of sodium hydrogen carbonate. For example, 100 ml of 0.5 N sodium hydrogen carbonate solution contains 0.05 mole of sodium hydrogen carbonate that is excessive. In addition, the carbon nano-tubes cannot contain 100% of —COOH. Evidenced by available documents, the carbon nano-tubes do not contain more than 10% of —COOH. However, should the amount of the carboxylic group be inadequate, errors such as errors of the amount of the sodium hydrogen carbonate and errors of the amount of the hydrochloric acid solution, the amount of the sodium hydrogen carbonate or the amount of the hydrochloric acid solution could be larger than the amount of the carboxylic group, and the carboxylic group could not be quantitatively analyzed. That is, the detection limit in the conventional acid-base titration is not low enough to conduct the quantitative analysis of a small amount of the carboxylic group. It is possible to make some progress such as conducting the experiment again to reduce the amount of the sodium hydrogen carbonate and increase the amount of the carbon nano-tubes, but the progress is limited.

The present invention is therefore intended to obviate or at least alleviate the problems encountered in prior art.

SUMMARY OF INVENTION

It is an objective of the present invention to provide a method for quantitatively analyzing a small number of a functional group on the surface of a solid material.

It is another objective of the present invention to provide a sensitive method for quantitatively analyzing a functional group on the surface of a solid material.

It is another objective of the present invention to provide an efficient method for quantitatively analyzing a functional group on the surface of a solid material.

To achieve the foregoing objectives, the method includes the step of introducing a first material that includes carbon nano-tubes and carboxylic group into sodium hydrogen carbonate solution for reaction, thus turning the carboxylic group into sodium carboxylate and consuming the sodium ions of the solution. Then, the carbon nano-tubes are separated from the sodium hydrogen carbonate solution by centrifugal filtration. Then, the change in the amount of the sodium ions in the sodium hydrogen carbonate solution before and after the reaction in the sodium hydrogen carbonate is analyzed. The amount of the sodium ions before the reaction minus the amount of the sodium ions after the reaction is the amount of the carboxylic group. Then, another sample of the first material is introduced into hydrochloric acid solution for reaction, thus turning the sodium carboxylate into the carboxylic group and dissolving the sodium ions in the hydrochloric acid solution. Then, the carbon nano-tubes are separated from the hydrochloric acid solution by centrifugal filtration. Finally, the amount of sodium ions before and after the reaction in the hydrochloric acid solution is analyzed. The amount of the sodium ions after the reaction in the hydrochloric acid solution minus the amount of the sodium ions before the reaction in the hydrochloric acid solution is the amount of the carboxylic group for confirming the result of the foregoing analysis.

Other objectives, advantages and features of the present invention will be apparent from the following description referring to the attached drawings.

BRIEF DESCRIPTION OF DRAWINGS

The present invention will be described via detailed illustration of the preferred embodiment referring to the drawing wherein:

FIG. 1 is a flow chart of a method for quantitatively analyzing a functional group on the surface of a solid material in accordance with the preferred embodiment of the present invention.

DETAILED DESCRIPTION OF PREFERRED EMBODIMENT

Referring to FIG. 1, there is shown a method for quantitatively analyzing a functional group on the surface of a solid material in accordance with the preferred embodiment of the present invention. The solid material is carbon nano-tubes for example. The functional group is carboxylic group for example. The method is based on acid-base titration.

(A) A first material 10 is introduced into sodium hydrogen carbonate solution 20 so that the first material 10 is turned into a second material 14. The first material 10 includes a first number (c) of moles of carboxylic group 12 boded to carbon nano-tubes 11. The sodium hydrogen carbonate solution 20 contains a second number (d) of moles of sodium hydrogen carbonate. The carboxylic group 12 reacts with the sodium hydrogen carbonate to produce sodium carboxylate 13 and consume the sodium ions of the sodium hydrogen carbonate solution 20. Therefore, the second material 14 includes the sodium carboxylate 13 attached to the carbon nano-tubes 11. To expedite the reaction, heating or an ultrasonic bath can be used. The sodium hydrogen carbonate solution 20 is sampled.

(B) After the reaction, the carbon nano-tubes 11 are separated from the sodium hydrogen carbonate solution 20 by centrifugal filtration. The solution includes the second number minus the first number (d–c) of mole of sodium hydrogen carbonate. As mentioned, the second material 14 includes the sodium carboxylate 13 attached to the carbon nano-tubes 11.

(C) The amount of the sodium ions contained in the sodium hydrogen carbonate solution 20 is measured before and after the reaction. The amount of the sodium ions is the second number (d) of moles. The amount of the sodium ions is the second number minus the first number (d–c) of moles. The amount (d) measured before the reaction minus the amount (d–c) measured after the reaction is the amount (c) of the carboxylic group 12.

(D) The second material 14, which includes the carbon nano-tubes 11 and the sodium carboxylate 13, is introduced into hydrochloric acid solution 30 for reaction. The sodium carboxylate 13 (c moles) carried on the carbon nano-tubes 11 is turned into carboxylic group 12 (c moles) so that the sodium ions (c moles) are dissolved in the hydrochloric acid solution 30. Again, the first material 10 is produced in the hydrochloric acid solution 30.

(E) The carbon nano-tubes 11 are separated from the hydrochloric acid solution 30 by centrifugal filtration. As mentioned, the first material 10 includes the carboxylic group 12 carried on the carbon nano-tubes 11.

(F) The amount of the sodium ions is measured before and after the reaction with the hydrochloric acid solution 30. The amount of the sodium ions measured after the reaction minus the amount of the sodium ions measured before the reaction is the amount (c moles) of the carboxylic group 12 for confirmation of the result of Step (C).

The analysis of the amount of the sodium ions in Steps (C) and (F) may be conducted in an instrument such as an inductively coupled plasma-atomic emission spectrometry ("ICP-AES"), an atomic absorption spectrometer ("AA"), an inductively coupled plasma-mass spectrometry ("ICP-MS") or an ion chromatography ("IC").

In use, for example, 0.01 mole of the first material 10 is introduced into sodium hydrogen carbonate solution 20 that contains 1 mole of sodium hydrogen carbonate for reaction. Thus, there is produced 0.01 mole of the second material 14 and 0.99 mole of sodium hydrogen carbonate. By the centrifugal filtration, the carbon nano-tubes are separated from the solution, which contains 0.99 mole of sodium hydrogen carbonate. An ICP-AES is used to analyze the amount of the sodium ions before and after the reaction in the sodium hydrogen carbonate solution. The amount of the sodium ions before the reaction minus the amount of the sodium ions after the reaction is the amount of the consumed sodium ions. That is, 1 mole minus 0.99 mole is 0.01 mole. Hence, it is learned that the number of the first material is 0.01 mole before the reaction. Furthermore, the 0.01 mole of the second material carbon nano-tube sodium carboxylate is introduced into 1 mole of hydrochloric acid for reaction. Thus, 0.01 mole of sodium ions is released from the surface of the carbon nano-tubes. Again, the centrifugal filtration is conducted, and the ICP-AES is used to analyze the amount of the sodium ions before and after the reaction with the hydrochloric acid. It is learned that the amount of the sodium ions is increased by 0.01. Thus, it can be confirmed that the amount of the first material is 0.01 mole.

In another example, 10 mg of carbon nano-tubes reacts with 2 ml of 0.1 M sodium hydrogen carbonate solution. Furthermore, 2 ml of 0.1 M sodium hydrogen carbonate is reserved as a sample. After the reaction, centrifugal filtration is conducted to separate the carbon nano-tubes from the solution. The carbon nano-tubes are washed. The filtered solution and the 2 ml of 0.1 M sodium hydrogen carbonate solution that is reserved are frozen and dried and then dissolved in 2 ml of water. The ICP-AES is used to analyze the amount of the sodium ions. It is learned that the concentration of the sodium ions in the reserved 2 ml of 0.1 M sodium hydrogen carbonate solution is 2080 ppm while the concentration of the sodium ions in the filtered solution is 1960 ppm. It is calculated that the concentration of the first material is 1.043 mmol/g. In addition, 9 mg of carbon nano-tube-based sodium carboxylate is introduced into 2 ml of 2 N hydrochloric acid for reaction. Then, by the centrifugal filtration, the carbon nano-tubes are separated from the solution. The carbon nano-tubes are washed. The filtered solution and 2 ml of 2 N hydrochloric acid are frozen and dried and then dissolved in 1 ml of water. The ICP-AES is used to analyze the amount of the sodium ions before and after the reaction with the hydrochloric acid. It is learned that the concentration of the sodium ions in the filtered solution is 212 ppm while the concentration of the sodium ions in the 2 ml of 2 N hydrochloric acid is 1.1 ppm. It is calculated that the conetration of the first material is 1.018 mmol/g.

As discussed above, in accordance with the present invention, the quantitative analysis of the functional group is conducted with the sensitive instrument to lower the detection limit to reduce the amounts of the samples. As the amounts of the samples are reduced and the centrifugal filtration is used, the period of time required for the analysis is reduced. Furthermore, more samples can be processed in the present invention than in the prior art. In the centrifugal filtration, the amount of samples that can synchronously be processed is determined by the size of a rotor of a centrifugal machine. A typical rotor includes at least 10 bores for receiving at least 10 test tubes. On the contrary, suction filtration devices used in the prior art are bulky. Not many suction filtration devices are used in a laboratory. Hence, not many samples can synchronously be processed in a laboratory. Finally, the inductively coupled plasma-atomic emission spectrometry ("ICP-AES") is used to analyze the amount of the sodium ions before and after the reactions. Such a device is often equipped with an automatic sample-feeding device to form an automatic system to process samples at high speed. Therefore, with the present invention, the weight of the samples is reduced, the sensitivity is increased, time is saved, and the speed is increased.

The present invention has been described via the detailed illustration of the preferred embodiment. Those skilled in the art can derive variations from the preferred embodiment without departing from the scope of the present invention. Therefore, the preferred embodiment shall not limit the scope of the present invention defined in the claims.

The invention claimed is:

1. A method for quantitative analyzing a functional group on the surface of a solid material based on acid-base titration, wherein the method includes the steps of:
   introducing that includes carbon nano-tubes and carboxylic group into sodium hydrogen carbonate solution for reaction, thus turning the carboxylic group into sodium carboxylate and consuming the sodium ions of the solution;
   separating the carbon nano-tubes from the sodium hydrogen carbonate solution by centrifugal filtration;
   analyzing the change in the amount of the sodium ions in the sodium hydrogen carbonate solution before and after the reaction in the sodium hydrogen carbonate, wherein the amount of the sodium ions before the reaction minus the amount of the sodium ions after the reaction is the amount of the carboxylic group;
   introducing the separated carbon nano-tube that includes carbon nano-tube and sodium carboxylate into hydrochloric acid solution for reaction, thus turning the sodium carboxylate into the carboxylic group and dissolving the sodium ions in the hydrochloric acid solution;
   separating the carbon nano-tubes from the hydrochloric acid solution by centrifugal filtration; and
   analyzing the amount of sodium ions before and after the reaction in the hydrochloric acid solution, wherein the amount of the sodium ions after the reaction in the hydrochloric acid solution minus the amount of the sodium ions before the reaction in the hydrochloric acid solution is the amount of the carboxylic group for confirming the result of the foregoing analysis wherein the solid material is carbon nano-tubes, the functional group is the carboxylic group.

2. The method for quantitative analyzing a functional group on the surface of a solid material in accordance with claim 1, wherein the analyses of the amount of the sodium ions steps are conducted by a device selected from the group consisting of an inductively coupled plasma-atomic emission spectrometry, an atomic absorption spectrometer, an inductively coupled plasma-mass spectrometry and an ion chromatography.

3. The method for quantitative analyzing a functional group on the surface of a solid material in accordance with claim 1, further including the step of heating to expedite the reaction in the sodium hydrogen carbonate solution.

4. The method for quantitative analyzing a functional group on the surface of a solid material in accordance with claim 1, further including the step of executing an ultrasonic bath to expedite the reaction in the sodium hydrogen carbonate solution.

* * * * *